(12) United States Patent
Gygi et al.

(10) Patent No.: US 7,501,286 B2
(45) Date of Patent: Mar. 10, 2009

(54) ABSOLUTE QUANTIFICATION OF PROTEINS AND MODIFIED FORMS THEREOF BY MULTISTAGE MASS SPECTROMETRY

(75) Inventors: Steven P. Gygi, Foxboro, MA (US); Scott Anthony Gerber, Brookline, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 323 days.

(21) Appl. No.: 10/781,047

(22) Filed: Feb. 17, 2004

(65) Prior Publication Data
US 2004/0229283 A1 Nov. 18, 2004

(51) Int. Cl.
*G01N 24/00* (2006.01)
(52) U.S. Cl. ..................................... 436/173
(58) Field of Classification Search ........................ None
See application file for complete search history.

(56) References Cited

U.S. PATENT DOCUMENTS

| 4,572,915 | A | 2/1986 | Crooks |
| 5,532,002 | A | 7/1996 | Story |
| 2002/0123055 | A1 | 9/2002 | Estell et al. |

FOREIGN PATENT DOCUMENTS

| WO | WO 00/11208 | 3/2000 |
| WO | WO 02/084250 A2 | 10/2002 |

OTHER PUBLICATIONS

Gerber et al. "Direct profiling of multiple enzyme activities in human cell lysates by affinity chromatography/electrospray Ionization mass spectrometry application to clinical enzymology", Anal. Chem. 2001, 73:1651-1657.*

Sannolo, et al., "Biomonitoring of Human Exposure to Methyl Bromide by Isotope Dilution Mass Spectrometry of Peptide Adducts", Journal of Mass Spectrometry, J. Mass Spectrom. 34, 1028-1032 (1999).

Zhou, et al., XP-002974320 "A systematic approach to the analysis of protein phosphorylation", Nature Biotechnology, Apr. 2001, vol. 19, pp. 375-378.

Vinale, et al., "Development of a Stable Isotope Dilution Assay for an Accurate Quantification of Protein-Bound $N\epsilon$ (1-Deoxy-D -fructos-1-yl)-L-lysine Using a $^{13}$C-Labeled Internal Standard", J. Agric. Food Chem, 1999, 47, 5084-5092.

Desiderio, "Mass spectrometric analysis of neuropeptidergic systems in the human pituitary and cerebrospinal fluid", Journal of Chromatography B, 731 (1999) 3-22.

Barr, et al., "Isotope dilution-mass spectrometric quantification of specific proteins: model application with apolipoprotein A-1", Clinical Chemistry 42:10, 1676-1682 (1996).

Goshe, et al., "Phosphoprotein Isotope-Coded Affinity Tag Approach for Isolating and Quantitating Phosphopeptides in Proteome-Wide Analyses", Anal. Chem. 2001, 73, 2578-2586.

Gygi, et al., "Quantitative analysis of complex protein mixtures using isotope-coded affinity tags", Nature Biotechnology, vol. 17, Oct. 1999, pp. 994-955.

* cited by examiner

*Primary Examiner*—Jon P Weber
*Assistant Examiner*—Bin Shen
(74) *Attorney, Agent, or Firm*—George W. Neuner; Gregory B. Butler, Esq.; Edwards Angell Palmer & Dodge LLP

(57) ABSTRACT

The invention provides reagents, kits and methods for detecting and/or quantifying proteins in complex mixtures, such as a cell lysate. The methods can be used in high throughput assays to profile cellular proteomes. In one aspect, the invention provides a peptide internal standard labeled with a stable isotope and corresponding in amino acid sequence to the amino acid sequence of a subsequence of a target polypeptide. In another aspect, the peptide internal standard is labeled at a modified amino acid residue and is used to determine the presence of, and/or quantitate the amount of a particular modified form of a protein.

18 Claims, 7 Drawing Sheets

* = stable isotope (e.g. $^{13}C$)

Native tryptic peptide

GFTALK

MW: 635.364

AQUA Internal Standard

GFTAL*K

MW: 641.364

ABSOLUTE QUANTIFICATION OF PROTEINS AND MODIFIED FORMS THEREOF BY MULTISTAGE MASS SPECTROMETRY

GOVERNMENT GRANTS

At least part of the work contained in this application was performed under government grant HG00041 from the National Institutes of Health, U.S. Department of Health and Human Services. The government may have certain rights in this invention.

RELATED APPLICATIONS

This application claims priority under 35 U.S.C. §120 to PCT/US02/025778, filed Aug. 14, 2002, published in English, which claims priority under 35 U.S.C. §119(e) to United States Provisional Application Ser. No. 60/312,279, filed Aug. 14, 2001.

FIELD OF THE INVENTION

This invention provides methods, reagents and kits for obtaining absolute quantification of proteins and their modifications directly from cell lysates. In particular, the invention provides peptide internal standards for use in high performance liquid chromatography (HPLC) with online detection by multistage mass spectrometry ($MS^n$).

BACKGROUND OF THE INVENTION

There is a need to provide novel methods for the quantification of proteins and modified proteins from cell lysates. The current standard for protein detection (quantification) is based on immunoreactive detection (Western analysis). However, this technique requires the availability of an appropriately specific antibody. In addition, many antibodies only recognize proteins in an unfolded (denatured) form, cross-reactivity can be severely limiting, and quantification is generally relative.

The development of methods and instrumentation for automated, data-dependent electrospray ionization (ESI) tandem mass spectrometry (MS/MS) in conjunction with microcapillary liquid chromatography (LC) and database searching has significantly increased the sensitivity and speed of the identification of gel-separated proteins. Microcapillary LC-MS/MS has been used successfully for the large-scale identification of individual proteins directly from mixtures without gel electrophoretic separation (Link et al., 1999; Opitek et al., 1997). However, while these approaches dramatically accelerate protein identification, quantities of the analyzed proteins cannot be easily determined, and these methods have not been shown to substantially alleviate the dynamic range problem also encountered by the 2DE/MS/MS approach. Therefore, low abundance proteins in complex samples are also difficult to analyze by the microcapillary LC/MS/MS method without their prior enrichment.

There is thus a need to provide methods for the accurate comparison of protein expression levels between cells in two different states, particularly for comparison of low abundance proteins.

Another methodology has recently been described. ICAT™ reagent technology makes use of a class of chemical reagents called isotope coded affinity tags (ICAT). These reagents exist in isotopically heavy and light forms which are chemically identical with the exception of eight deuterium or hydrogen atoms, respectively. Proteins from two cells lysates can be labeled independently with one or the other ICAT reagent at cysteinyl residues. After mixing and proteolysing the lysates, the ICAT-labeled peptides are isolated by affinity to a biotin molecule incorporated into each ICAT reagent. ICAT-labeled peptides are analyzed by LC-MS/MS where they elute as heavy and light pairs of peptides. Quantification is performed by determining the relative expression ratio relating to the amount of each ICAT-labeled peptide pair in the sample.

Identification of each ICAT-labeled peptide is performed by a second stage of mass spectrometry (MS/MS) and sequence database searching. The end result is relative protein expression ratios on a large scale. The major drawback to this technique are 1) quantification is only relative; 2) specialized chemistry is required, and 3) database searches are hindered by the presence of the large ICAT reagent molecule, and 4) relative amounts of posttranslationally modified (e.g., phosphorylated) proteins are transparent to analysis.

SUMMARY

The present invention provides reagents, kits, and methods for accurate quantification of proteins and methods for using the same. The reagents, kits, and methods of the invention are useful for rapid, high throughput analysis of proteomes.

In one aspect, the invention provides a method for generating a peptide internal standard. The method comprises identifying a real or predicted peptide digestion product of a target polypeptide, determining the amino acid sequence of the peptide digestion product and synthesizing a peptide having the amino acid sequence. The peptide is labeled with a mass-altering label (e.g., by incorporating labeled amino acid residues during the synthesis process) and fragmented (e.g., by multi-stage mass spectrometry). Preferably, the label is a stable isotope. A peptide signature diagnostic of the peptide is determined, after one or more rounds of fragmenting, and the signature is used to identify the presence and/or quantity of a peptide of identical amino acid sequence in a sample.

Preferably, a labeled peptide is provided which co-elutes with an unlabeled peptide having the same amino acid sequence (i.e., a target peptide) in a chromatographic separation procedure (e.g., such as HPLC).

In one aspect, the mass-altering label is part of a peptide comprising a modification, and the peptide is fragmented to determine a peptide signature diagnostic of such a modified peptide. The modified residue in the peptide internal standard comprises a phosphorylated residue, a glycosylated residue, an acetylated residue, a ubiquitinated residue, a ribosylated residue, or a farnesylated residue, or another modification found in a cellular protein. In one aspect, panels of peptide internal standards are generated corresponding to (i.e., diagnostic of) different modified forms of the same protein.

Peptide internal standards corresponding to different peptide subsequences of a single target protein also can be generated to provide for redundant controls in a quantitative assay. In one aspect, different peptide internal standards corresponding to the same target protein are generated and differentially labeled (e.g., peptides are labeled at multiple sites to vary the amount of heavy label associated with a given peptide).

In another aspect, a panel of peptide internal standards corresponding to different amino acid subsequences of a single protein is used to scan for mutations in that protein. In a further aspect, peptide internal standards corresponding to different variant sequences of a single amino acid subsequence of a single protein are provided. A match between a peptide internal standard and a target peptide in a sample indicates the presence of a variant sequence in the sample. In one aspect, the multiple peptide internal standards corresponding to variant sequences are differentially labeled.

In a further aspect, a panel of peptide internal standards corresponding to amino acid subsequences of different proteins in a molecular pathway is generated. Molecular pathways, include, but are not limited to signal transduction pathways, cell cycle pathways, metabolic pathways, blood clotting pathways, and the like. In one aspect, the panel includes peptide standards which correspond to different modified forms of one or more proteins in a pathway and the panel is used to determine the presence and/or quantity of the activated or inactivated form of a pathway protein.

The invention also provides a method for determining the presence and/or quantity of a target polypeptide in at least one mixture of different polypeptides. The method comprises providing a mixture of different polypeptides and spiking the mixture with a known quantity of a peptide internal standard labeled with a mass-altering label. Preferably, the labeled peptide internal standard comprises a subsequence of the target polypeptide and possesses a known peptide fragment signature diagnostic of the presence of the peptide subsequence. The spiked mixture is treated with a protease activity to generate a plurality of peptides including the labeled peptide internal standard and peptides corresponding to the target polypeptide. Preferably, a chromatographic separation step is performed to isolate the labeled peptide internal standard and any target peptide present in the spiked mixture which comprises the same amino acid sequence as the standard. Preferably, the internal standard and target peptide co-elute with each other.

The labeled peptide internal standard and target peptide are fragmented (e.g., using multistage mass spectrometry) and the ratio of labeled fragments to unlabeled fragments; is determined. The quantity of the target polypeptide can be calculated using both the ratio and known quantity of the labeled internal standard. The mixtures of different polypeptides can include, but are not limited to, such complex mixtures as a crude fermenter solution, a cell-free culture fluid, a cell or tissue extract, blood sample, a plasma sample, a lymph sample, a cell or tissue lysate; a mixture comprising at least about 100 different polypeptides; at least about 1000 different polypeptides, at least about 100,000 different polypeptides. or a mixture comprising substantially the entire complement of proteins in a cell or tissue. In one preferred aspect, the method is used to determine the presence of and/or quantity of one or more target polypeptides directly from one or more cell lysates, i.e., without separating proteins from other cellular components or eliminating other cellular components.

In one aspect, the presence and/or quantity of target polypeptide in a mixture are diagnostic of a cell state. In another aspect, the cell state is representative of an abnormal physiological response, for example, a physiological response which is diagnostic of a disease. In a further aspect, the cell state is a state of differentiation or represents a cell which has been exposed to a condition or agent (e.g., a drug, a therapeutic agent, a potential toxin). In one aspect, the method is used to diagnose the presence or risk of a disease. In another aspect, the method is used to identify a condition or agent which produces a selected cell state (e.g., to identify an agent which returns one or more diagnostic parameters of a cell state to normal).

In a further aspect, the method comprises determining the presence and/or quantity of target peptides in at least two mixtures. In another aspect, one mixture is from a cell having a first cell state and the second mixture is from a cell having a second cell state. In a further aspect, the first cell is a normal cell and the second cell is from a patient with a disease. In still a further aspect, the first cell is exposed to a condition and/or treated with an agent and the second cell is not exposed and/or treated. Preferably, first and second mixtures are evaluated in parallel.

Alternatively, the two mixtures can be from identical samples or cells. In one aspect, a labeled peptide internal standard is provided in different known amounts in each mixture. In another aspect, pairs of labeled peptide internal standards are provided each comprising mass-altering labels which differ in mass, e.g., by including different amounts of a heavy isotope in each peptide.

The invention also provides a method of determining the presence of and/or quantity of a modification in a target polypeptide. Preferably, the label in the internal standard is part of a peptide comprising a modified amino acid residue or to an amino acid residue which is predicted to be modified in a target polypeptide. In one aspect, the presence of the modification reflects the activity of a target polypeptide and the assay is used to detect the presence and/or quantity of an active polypeptide. The method is advantageous in enabling detection of small quantities of polypeptide (e.g., about 1 part per million (ppm) or less than about 0.001% of total cellular protein).

The invention additionally provides a method for scanning for mutations in a protein sequence using panels of peptide internal standards corresponding to different variant forms of a single sequence or multiple peptide internal standards representing different amino acid subsequences of a protein. In the first scenario, a match to a variant peptide internal standard in a sample indicates the presence of the variant in the sample. In the second scenario, a lack of match to a one peptide internal standard and matches to one or more other peptide internal standards indicates the presence of a mutation in the amino acid sequence corresponding to the mismatched peptide.

In a further aspect, the invention provides a method for profiling the activity of a molecular pathway using panels of peptide internal standards corresponding to different pathway proteins and/or to different modified forms of the proteins. The presence and/or quantity of the proteins can be used to profile the function of a pathway in a particular cell. In one aspect, the pathway is one or more of a signal transduction pathway, a cell cycle pathway, a metabolic pathway, a blood clotting pathway and the like. The coordinate function of multiple pathways can be evaluated using a plurality of panels of standards. Similarly, the peptide internal standards can be used to assay for the presence of multiple diseases or pathological conditions by providing a panel of peptide internal standards which comprises peptide internal standards diagnostic of different diseases.

The invention further provides reagents useful for performing the method. In one aspect, a reagent according to the invention comprises a peptide internal standard labeled with a stable isotope. Preferably, the standard has a unique peptide fragmentation signature diagnostic of the peptide. The peptide is a subsequence of a known protein and can be used to identify the presence of and/or quantify the protein in sample, such as a cell lysate. In one aspect, the peptide internal standard comprises a label associated with a modified amino acid residue, such as a phosphorylated amino acid residue, a glycosylated amino acid residue, an acetylated amino acid residue, a farnesylated residue, a ribosylated residue, and the like. In another aspect, a pair of reagents is provided, a peptide internal standard corresponding to a modified peptide and a peptide internal standard corresponding to a peptide identical in sequence but not modified.

In one aspect, panels of peptide internal standards representing different variant forms of a single amino acid subsequence of a polypeptide are provided.

In another aspect, panels of peptide internal standards corresponding to different amino acid subsequences of single polypeptide are provided.

In a further aspect, panels of peptide internal standards are provided which correspond to different proteins in a molecular pathway (e.g., a signal transduction pathway, a cell cycle pathway, a metabolic pathway, a blood clotting pathway and the like). In still a further aspect, peptide internal standards corresponding to different modified forms of one or more proteins in a pathway are provided.

In still a further aspect, panels of peptide internal standards are provided which correspond to proteins diagnostic of different diseases, allowing a mixture of peptide internal standards to be used to test for the presence of multiple diseases in a single assay.

The invention additionally provides kits comprising one or more peptide internal standards labeled with a stable isotope. In one aspect, a kit comprises peptide internal standards comprising different peptide subsequences from a single known protein. In another aspect, the kit comprises peptide internal standards corresponding to different variant forms of the same amino acid subsequence of a target polypeptide. In still another aspect, the kit comprises peptide internal standards corresponding to different known or predicted modified forms of a polypeptide. In a further aspect, the kit comprises peptide internal standards corresponding to sets of related proteins, e.g., such as proteins involved in a molecular pathway (a signal transduction pathway, a cell cycle, etc) and/or to different modified forms of proteins in the pathway. In still a further aspect, a kit comprises a labeled peptide internal standard as described above and software for performing multistage mass spectrometry. The kit may also include a means for obtaining access to a database comprising data files which include data relating to the mass spectra of fragmented peptide ions generated from peptide internal standards. The means for obtaining access can be provided in the form of a URL and/or identification number for accessing a database or in the form of a computer program product comprising the data files. In one aspect, the kit comprises a computer program product which is capable of instructing a processor to perform any of the methods described above.

BRIEF DESCRIPTION OF THE FIGURES

The objects and features of the invention can be better understood with reference to the following detailed description and accompanying drawings.

FIG. 3A shows a signature obtained after a second stage of mass spectrometry.

FIG. 4A shows sample processing steps in which a cell lysate is spiked with a known amount of a labeled peptide internal standard according to the invention.

DETAILED DESCRIPTION

Figure 1:
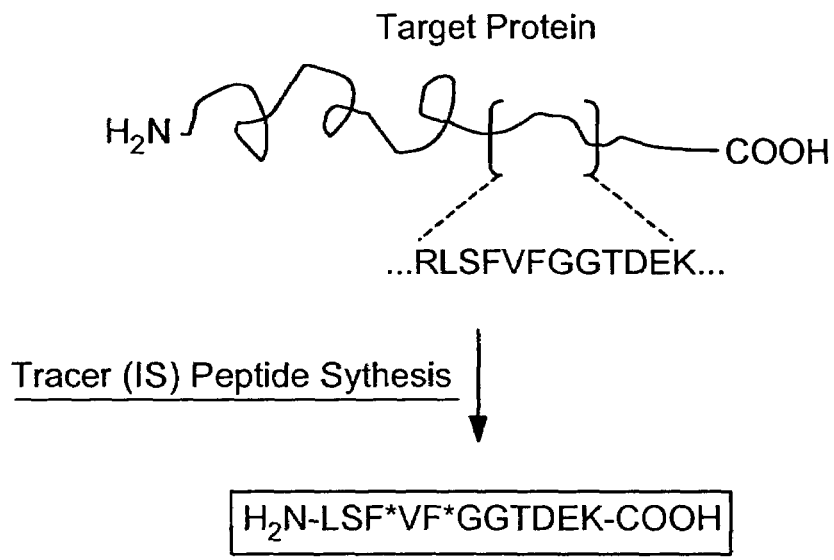
FIG. 1 is a schematic diagram illustrating a method for generating a peptide internal standard for a protein or modified protein to be detected and/or quantified (Peptides shown are disclosed as SEQ ID NOS 4 and 5, respectively in order of appearance).

The invention provides reagents, kits and methods for detecting and/or quantifying proteins in complex mixtures, such as a cell lysate. The methods can be used in high through put assays to profile cellular proteomes.

Definitions

The following definitions are provided for specific terms which are used in the following written description.

As used in the specification and claims, the singular form "a", "an" and "the" include plural references unless the context clearly dictates otherwise. For example, the term "a cell" includes a plurality of cells, including mixtures thereof. The term "a protein" includes a plurality of proteins.

"Protein", as used herein, means any protein, including, but not limited to peptides, enzymes, glycoproteins, hormones, receptors, antigens, antibodies, growth factors, etc., without limitation. Presently preferred proteins include those comprised of at least 25 amino acid residues, more preferably at least 35 amino acid residues and still more preferably at least 50 amino acid residues. The terms "polypeptide" and "protein" are generally used interchangeably herein to refer to a polymer of amino acid residues.

As used herein, the term "peptide" refers to a compound of two or more subunit amino acids. The subunits are linked by peptide bonds.

As used herein, a "target protein" or a "target polypeptide" is a protein or polypeptide whose presence or amount is being determined in a protein sample. The protein/polypeptide may be a known protein (i.e., previously isolated and purified) or a putative protein (i.e., predicted to exist on the basis of an open reading frame in a nucleic acid sequence).

As used herein, a "protease activity" is an activity which cleaves amide bonds in a protein or polypeptide. The activity may be implemented by an enzyme such as a protease or by a chemical agent, such as CNBr.

As used herein, "a protease cleavage site" is an amide bond which is broken by the action of a protease activity.

As used herein, a "labeled peptide internal standard" refers to a synthetic peptide which corresponds in sequence to the amino acid subsequence of a known protein or a putative protein predicted to exist on the basis of an open reading frame in a nucleic acid sequence and which is labeled by a mass-altering label such as a stable isotope. The boundaries of a labeled peptide internal standard are governed by protease cleavage sites in the protein (e.g., sites of protease digestion or sites of cleavage by a chemical agent such as CNBr). Protease cleavage sites may be predicted cleavage sites (determined based on the primary amino acid sequence of a protein and/or on the presence or absence of predicted protein modifications, using a software modeling program) or may be empirically determined (e.g., by digesting a protein and sequencing peptide fragments of the protein). In one aspect, a labeled peptide internal standard includes a modified amino acid residue.

"Percent identity" and "similarity" between two sequences can be determined using a mathematical algorithm (see, e.g., *Computational Molecular Biology*, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991). For example, the percent identity between two amino acid sequences can be determined using the Needleman and Wunsch algorithm (J. Mol. Biol. (48): 444-453, 1970) which is part of the GAP program in the GCG software package (available at http://www.gcg.com), by the local homology algorithm of Smith & Waterman (Adv. Appl. Math. 2: 482, 1981), by the search for similarity methods of Pearson & Lipman (Proc. Natl. Acad. Sci. USA 85: 2444, 1988) and Altschul, et al. (Nucleic Acids Res. 25(17): 3389-3402, 1997), by computerized implementations of these algorithms (GAP, BESTFIT, FASTA, and BLAST in the Wisconsin Genetics Software Package (available from, Genetics Computer Group, 575 Science Dr., Madison, Wis.), or by manual alignment and visual inspection (see, e.g., Ausubel et al., supra). Gap parameters can be modified to suit a user's needs. For example, when employing the GCG software package, a NWSgapdna.CMP matrix and a gap weight of 40, 50, 60, 70, or 80 and a length weight of 1, 2, 3, 4, 5, or 6 can be used. Examplary gap weights using a Blossom 62 matrix or a PAM250 matrix, are 16, 14, 12, 10, 8, 6, or 4, while exemplary length weights are 1, 2, 3, 4, 5, or 6. The percent identity between two amino acid or nucleotide sequences also can be determined using the algorithm of E. Myers and W. Miller (CABIOS 4: 11-17, 1989) which has been incorporated into the ALIGN program (version 2.0), using a PAM120 weight residue table, a gap length penalty of 12 and a gap penalty of 4.

As used herein, "a peptide fragmentation signature" refers to the distribution of mass-to-charge ratios of fragmented peptide ions obtained from fragmenting a peptide, for example, by collision induced disassociation, ECD, LID, PSD, IRNPD, SID, and other fragmentation methods. A peptide fragmentation signature which is "diagnostic" or a "diagnostic signature" of a target protein or target polypeptide is one which is reproducibly observed when a peptide digestion product of a target protein/polypeptide identical in sequence to the peptide portion of a peptide internal standard, is fragmented and which differs only from the fragmentation pattern of the peptide internal standard by the mass of the mass-altering label. Preferably, a diagnostic signature is unique to the target protein (i.e., the specificity of the assay is at least about 95%, at least about 99%, and preferably, approaches 100%).

A "relational" database as used herein means a database in which different tables and categories of the database are related to one another through at least one common attribute and is used for organizing and retrieving data.

The term "external database" as used herein refers to publicly available databases that are not a relational part of the internal database, such as GenBank and Blocks.

As used herein, an "expression profile" refers to measurement of a plurality of cellular constituents that indicate aspects of the biological state of a cell. Such measurements may include, e.g., abundances or proteins or modified forms thereof.

As used herein, a "cell state profile" refers to values of measurements of levels of one or more proteins in the cell. Preferably, such values are obtained by determining the amount of peptides in a sample having the same peptide fragmentation signatures as that of peptide internal standards corresponding to the one or more proteins. A "diagnostic profile" refers to values that are diagnostic of a particular cell state, such that when substantially the same values are observed in a cell, that cell may be determined to have the cell state. For example, in one aspect, a cell state profile comprises the value of a measurement of p53 expression in a cell. A diagnostic profile would be a value which is significantly higher than the value determined for a normal cell and such a profile would be diagnostic of a tumor cell. A "test cell state profile" is a profile which is unknown or being verified.

As used herein, a processor that "receives a diagnostic profile" receives data relating to the values diagnostic of a particular cell state. For example, the processor may receive the values by accessing a database where such values are stored through a server in communication with the processor.

Labeled Peptide Internal Standards

The invention provides labeled peptide internal standards for use in determining the presence of, and/or quantifying the amount of, a target protein in a sample which comprises an amino acid subsequence identical to the peptide portion of the internal standard. Peptide internal standards are generated by examining the primary amino acid sequence of a protein and synthesizing a peptide comprising the same sequence as an amino acid subsequence of the protein (see, e.g., FIG. 1). In one aspect, the peptide's boundaries are determined by predicting the cleavage sites of a protease. In another aspect, a protein is digested by the protease and the actual sequence of one or more peptide fragments is determined. Suitable proteases include, but are not limited to one or more of: serine proteases (e.g., such as trypsin, hepsin, SCCE, TADG12, TADG14); metallo proteases (e.g., such as PUMP-1); chymotrypsin; cathepsin; pepsin; elastase; pronase; Arg-C; Asp-N; Glu-C; Lys-C; carboxypeptidases A, B, and/or C; dispase; thermolysin; cysteine proteases such as gingipains, and the like. Proteases may be isolated from cells or obtained through recombinant techniques. Chemical agents with a protease activity also can be used (e.g., such as CNBr).

The target protein can be a known protein or a protein predicted to exist on the basis of an open reading frame in a nucleic acid sequence. Such open reading frames can be identified from a database of sequences including, but not limited to, the GenBank database, EMBL data library, the Protein Sequence Database and PIR-International, SWISS-PROT, The ExPASy proteomics server of the Swiss Institute of Bioinformatics (SIB) and databases described in PCT/US01/25884. Predicted cleavage sites also can be identified through modeling software, such as IVIS-Digest (available at http://prospector.ucsf.edu/). Predicted sites of protein modification also can be determined using software packages such as Scansite, Findmod, NetOGlyc (for prediction of type-O-glycosylation sequences), YinOYang (for prediction of O-beta-GlcNac attachment sites), big-PI Predictor (for prediction of GPI modifications), NetPhos (for prediction of Ser, Thr, and Tyr phosphorylation sites), NMT (for prediction of N-terminal N-myristolation) and Sulfinator (for prediction of tyrosine sulfation sites) which are accessible through http://au.expasy.org/tools/#ptm, for example.

A peptide sequence within a target protein is selected according to one or more criteria to optimize the use of the peptide as an internal standard. Preferably, the size of the peptide is selected to minimize the chances that the peptide sequence will be repeated elsewhere in other non-target proteins. Preferably, therefore, a peptide is at least about 6 amino acids. The size of the peptide is also optimized to maximize ionization frequency. Thus, peptides longer than about 20 amino acids are not preferred. In one aspect, an optimal peptide ranges from about 6 amino acids to about 20 amino acids, and preferably from about 7 amino acids to about 15 amino acids.

A peptide sequence is also selected which is not likely to be chemically reactive during mass spectrometry. Thus, peptide sequences which comprise cysteine, tryptophan or methionine residues are avoided.

Peptides also are selected based on the presence of one or more bonds that preferentially fragment. For example, because peptides will preferentially fragment at proline residues, intense fragment ions may be produced at proline. Therefore in one aspect of the invention, a peptide is selected from a region of a protein comprising a proline amino acid residue.

Figure 5A:
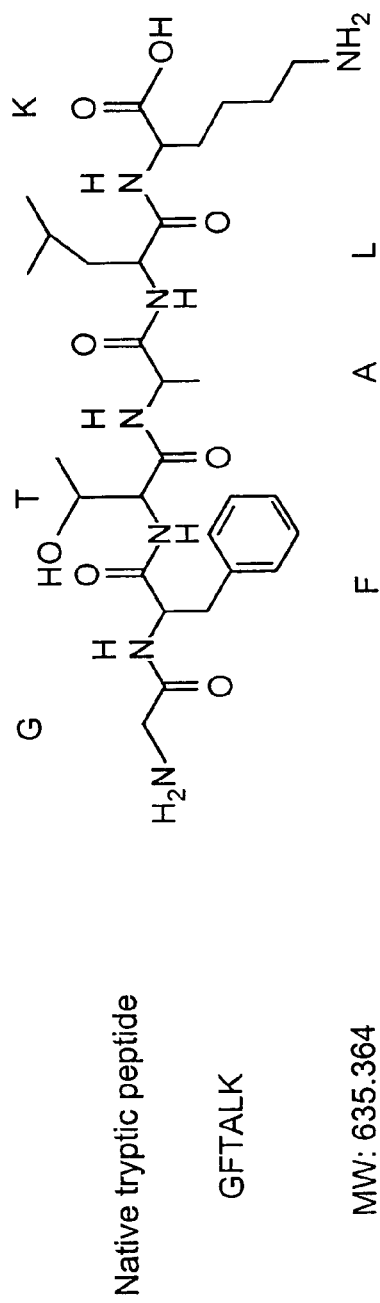
FIG. 5A shows a peptide internal standard suitable for use in detecting and/or quantitating a protein comprising the amino acid sequence GFTALK (SEQ ID NO: 1). The upper panel of the Figure shows the native tryptic peptide. The lower portion of the FIG. shows a peptide internal standard corresponding to this peptide which comprises a stable isotope ($^{13}C$). As can be seen from the Figure, the stable isotope provides a characteristic mass difference in the two peptides without altering the essential chemical structure of the peptide.
Figure 5A:
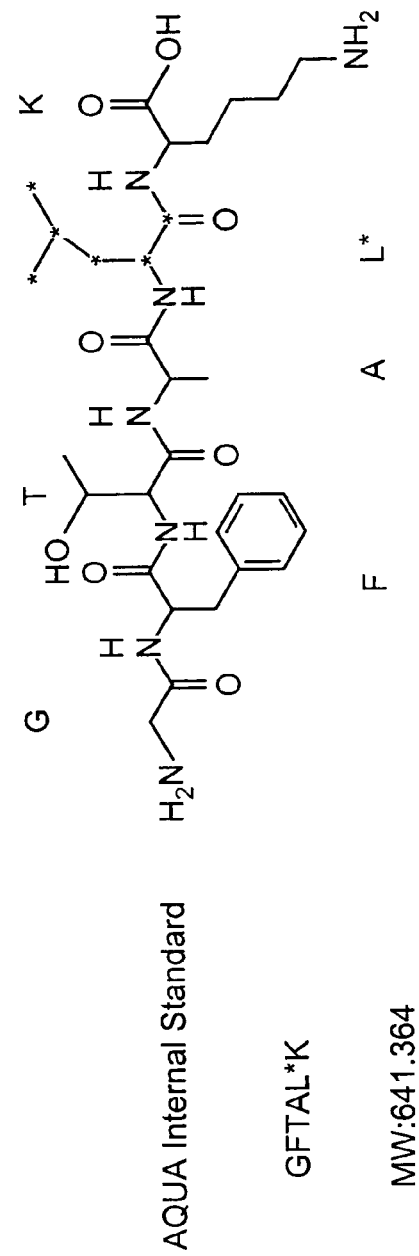
Figure 5B:
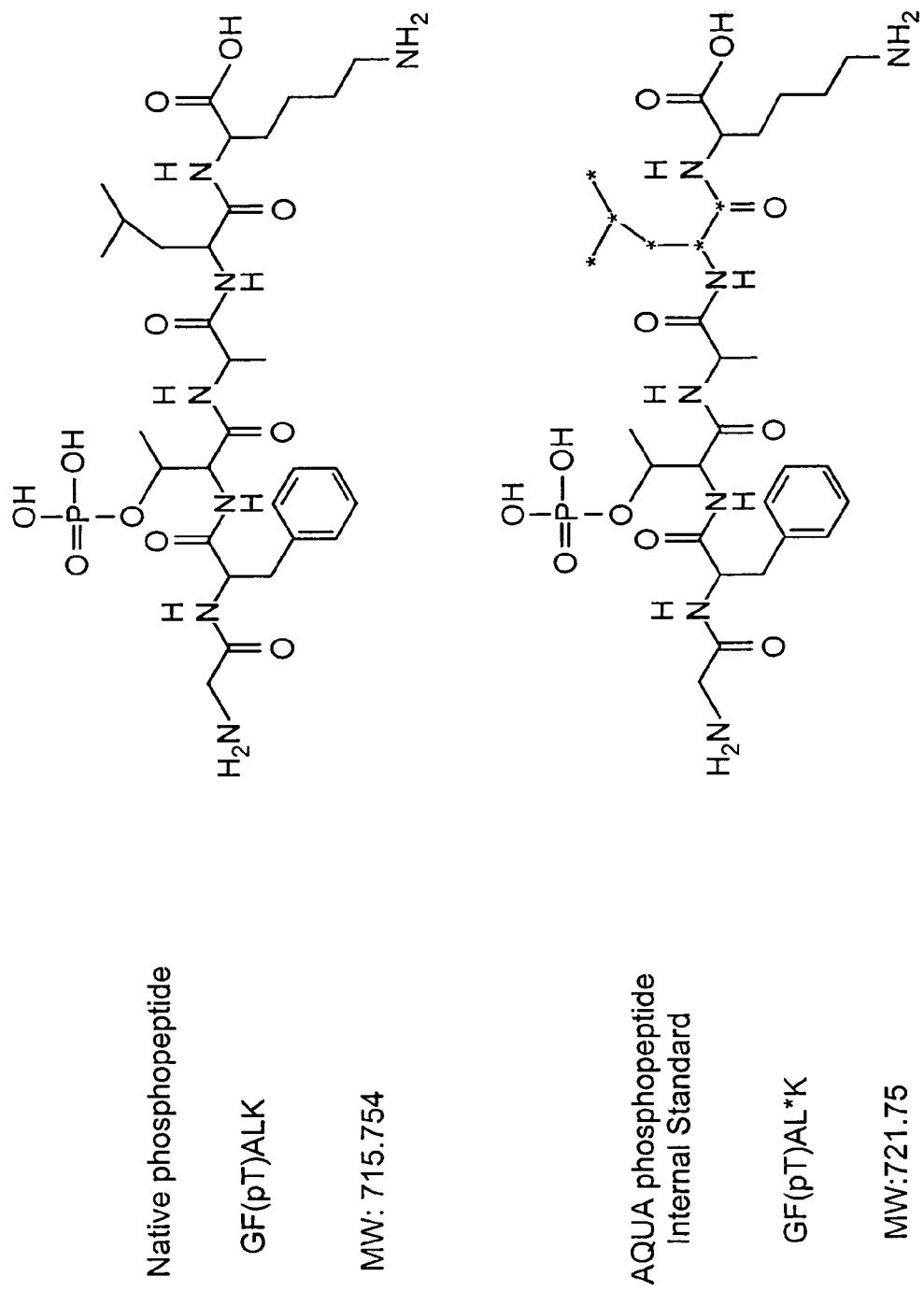
FIG. 5B shows a peptide internal standard suitable for use in detecting a phosphorylated form of a protein comprising the amino acid sequence GFTALK (SEQ ID NO: 1).
Figure 5C:
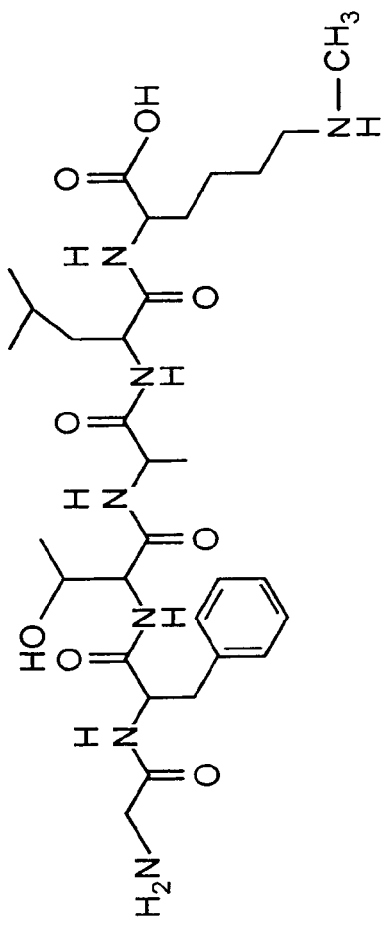
FIG. 5C shows a peptide internal standard suitable for use in detecting a methylated form of the amino acid sequence GFTALK (SEQ ID NO: 1).
Figure 5C:
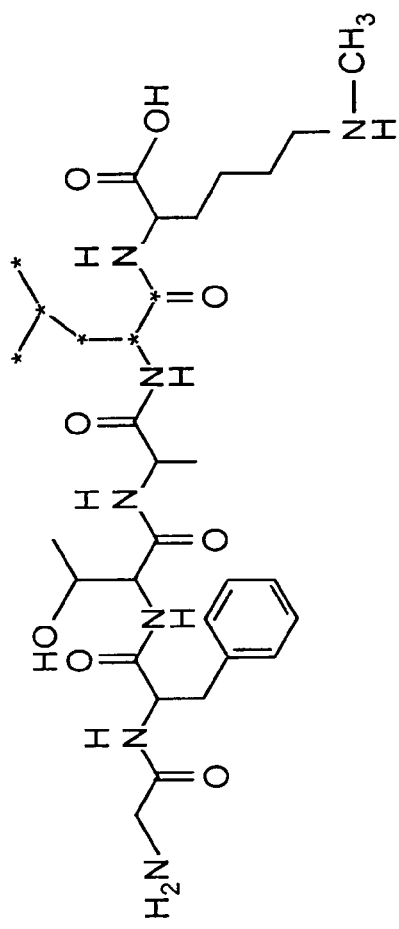

In another aspect, a peptide is selected from a region of a protein which is not expected or not known to be modified, so that the peptide internal standard can be used to determine the quantity of all forms of the protein. However, in a further aspect, the peptide internal standard does include an amino acid residue which is expected to, or is known to be modified, to provide an internal standard to quantify only the modified form the protein (see, e.g., FIGS. 5B and 5C). Peptide standards representing modified (e.g., FIGS. 5B and 5C) and unmodified forms of a protein (see, e.g., FIG. 5A) can be used together, to determine the extent of protein modification in a particular sample of proteins, i.e., to determine what fraction of the total amount of protein is represented by the modified form.

The peptide is synthesized using one or more labeled amino acids (i.e., the label is actually part of the peptide) or less preferably, labels may be attached after synthesis. By providing the label as part of the peptide (see, e.g., FIGS. 5A-5C), there are minimal differences in the chemical structure of a peptide internal standard and a native peptide obtained from the digestion of a target protein with a protease activity. Further, because the peptide is synthesized, it is unnecessary to separate and/or purify the peptide from other cellular proteins.

Preferably, the label is a mass-altering label. The type of label selected is generally based on the following considerations: The mass of the label should preferably be unique to shift fragment masses produced by MS analysis to regions of the spectrum with low background. The ion mass signature component is the portion of the labeling moiety which preferably exhibits a unique ion mass signature in mass spectrometric analyses. The sum of the masses of the constituent atoms of the label is preferably uniquely different than the fragments of all the possible amino acids. As a result, the labeled amino acids and peptides are readily distinguished from unlabeled amino acids and peptides by their ion/mass pattern in the resulting mass spectrum. In a preferred embodiment, the ion mass signature component imparts a mass to a protein fragment produced during mass spectrometric fragmentation that does not match the residue mass for any of the 20 natural amino acids.

The label should be robust under the fragmentation conditions of MS and not undergo unfavorable fragmentation. Labeling chemistry should be efficient under a range of conditions, particularly denaturing conditions and the labeled tag preferably remains soluble in the MS buffer system of choice. Preferably, the label does not suppress the ionization efficiency of the protein. More preferably, the label does not alter the ionization efficiency of the protein and is not otherwise chemically reactive. Alternatively, or additionally, the label contains a mixture of two or more isotopically distinct species to generate a unique mass spectrometric pattern at each labeled fragment position.

In one preferred aspect, peptide internal standards comprise mass-altering labels which are stable isotopes. In certain preferred embodiments, the method utilizes isotopes of hydrogen, nitrogen, oxygen, carbon, or sulfur. Suitable isotopes include, but are not limited to, $^2H$, $^{13}C$, $^{15}N$, $^{17}O$, $^{18}O$, or $^{34}S$. In another aspect, pairs of peptide internal standards can be provided, comprising identical peptide portions but distinguishable labels, e.g., peptides may be labeled at multiple sites to provide different heavy forms of the peptide). Multiple labeled amino acids may be incorporated in a peptide during the synthesis process. In another aspect, the label is part of a peptide comprising a modified amino acid residue, such as a phosphorylated residue (see, e.g., FIG. 5B), a glycosylated residue, an acetylated residue, a ribosylated residue, or a farnesylated residue, a methlyated residue (see, e.g., FIG. 5C). In this embodiment, pairs or larger sets of peptide internal standards corresponding to modified and unmodified peptides also can be produced. In one aspect, such a pair/set is differentially labeled.

Figure 2:
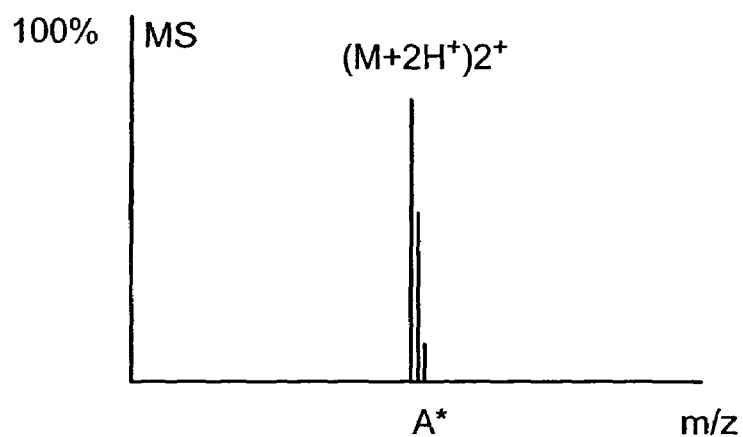
FIG. 2 illustrates characterization of peptide internal standards by mass-to-charge ratio and retention time in reverse phase chromatography according to one aspect of the invention.

Peptide internal standards are characterized according to their mass-to-charge ratio (m/z) and preferably, also according to their retention time on a chromatographic column (e.g., such as an HPLC column). Internal standards are selected which co-elute with peptides of identical sequence but which are not labeled (see, e.g., FIG. 2).

The peptide internal standard is then analyzed by fragmenting the peptide. Fragmentation can be achieved by inducing ion/molecule collisions by a process known as collision-induced dissociation (CID) (also known as collision-activated dissociation (CAD)). Collision-induced dissociation is accomplished by selecting a peptide ion of interest with a mass analyzer and introducing that ion into a collision cell. The selected ion then collides with a collision gas (typically argon or helium) resulting in fragmentation. Generally, any method that is capable of fragmenting a peptide is encompassed within the scope of the present invention. In addition to CID, other fragmentation methods include, but are not limited to, surface induced dissociation (SID) (James and Wilkins, Anal. Chem. 62: 1295-1299, 1990; and Williams, et al., J Amer. Soc. Mass Spectrom. 1: 413-416, 1990), blackbody infrared radiative dissociation (BIRD); electron capture dissociation (ECD) (Zubarev, et al., J. Am. Chem. Soc. 120: 3265-3266, 1998); post-source decay (PSD), LID, and the like.

The fragments are then analyzed to obtain a fragment ion spectrum. One suitable way to do this is by CID in multistage mass spectrometry ($MS^n$). Traditionally used to characterize the structure of a peptide and/or to obtain sequence information, it is a discovery of the present invention, that $MS^n$ provides enhanced sensitivity in methods for quantitating absolute amounts of proteins. Thus, in one aspect, peptide internal standards are generated for low abundance proteins (e.g., below 2000 copies/cell).

Figure 3A:
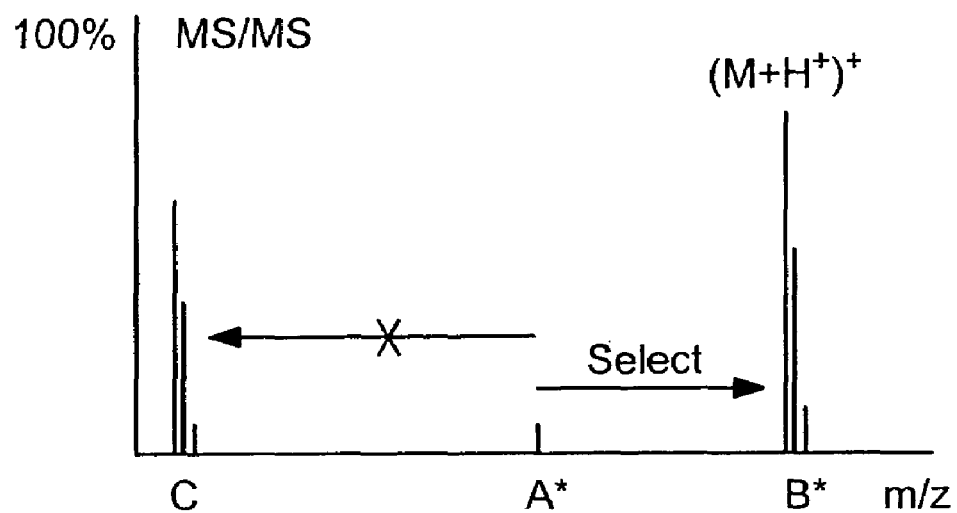
FIGS. 3A and B show characterization of a peptide signature by multistage mass spectrometry.
Figure 3B:
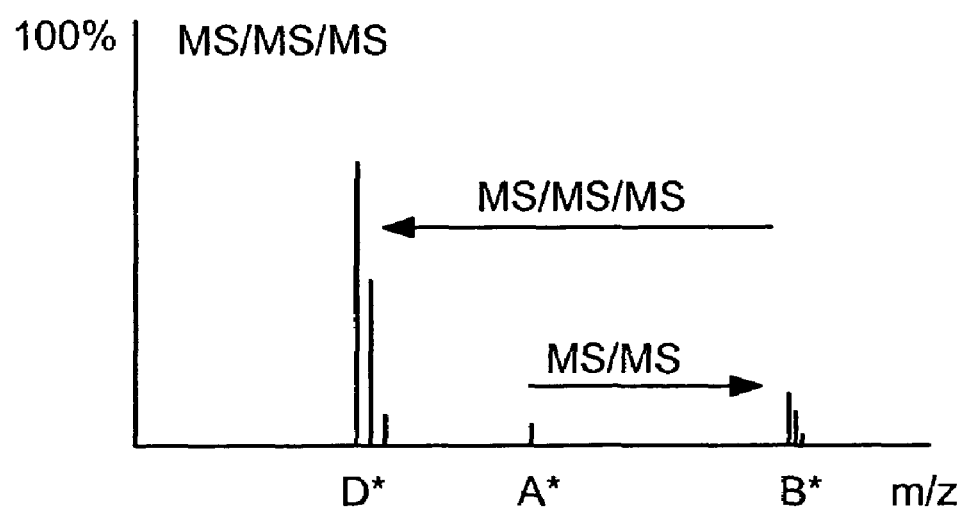
FIG. 3B shows a signature obtained after performing a third stage of mass spectrometry.

Preferably, a peptide internal standard is analyzed by at least two stages of mass spectrometry to determine the fragmentation pattern of the peptide and to identify a peptide fragmentation signature (see, e.g., FIG. 3A). More preferably, a peptide signature is obtained in which peptide fragments have significant differences in m/z ratios to enable peaks corresponding to each fragment to be well separated. Still more preferably, signatures are unique, i.e., diagnostic of a peptide being identified and comprising minimal overlap with fragmentation patterns of peptides with different amino acid sequences. If a suitable fragment signature is not obtained at the first stage, additional stages of mass spectrometry are performed until a unique signature is obtained (see, e.g., FIG. 3B).

Fragment ions in the MS/MS and $MS^3$ spectra are generally highly specific and diagnostic for peptides of interest. In contrast, to prior art methods, the identification of peptide diagnostic signatures provides for a way to perform highly selective analysis of a complex protein mixture, such as a cellular lysate in which there may be greater than about 100, about 1000, about 10,000, or even about 100,000 different kinds of proteins. Thus, while conventional mass spectroscopy would not be able to distinguish between peptides with different sequences but similar m/z ratios (which would tend to co-elute with any labeled standard being analyzed), the use of peptide fragmentation methods and multistage mass spectrometry in conjunction with LC methods, provide a way to detect and quantitate target proteins which are only a small fraction of a complex mixture (e.g., present in less than 2000 copies per cell or less than about 0.001% of total cellular protein) through these diagnostic signatures.

Figure 6:
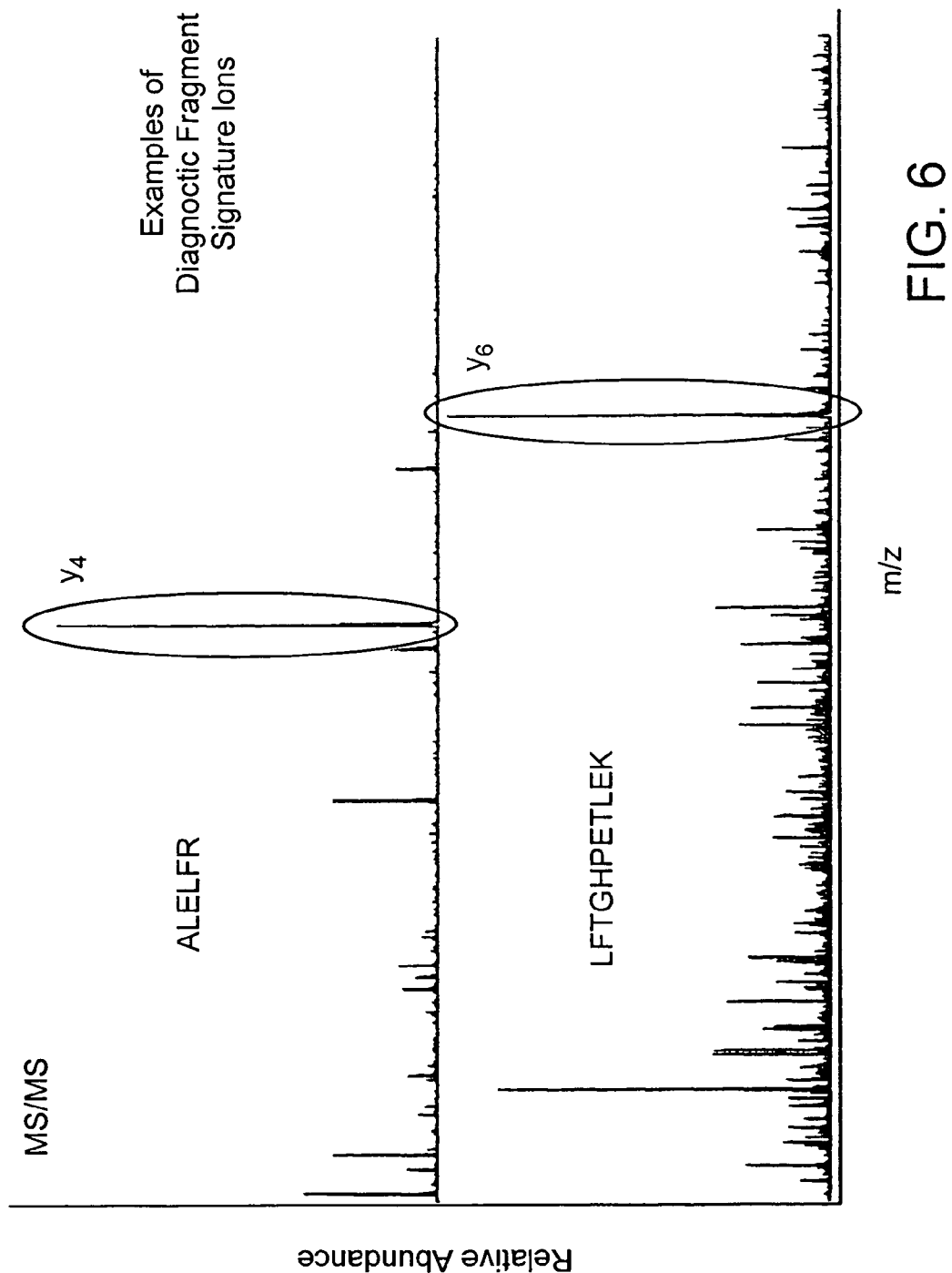
FIG. 6 shows diagnostic peptide fragmentation signatures obtained for two peptides comprising the sequences ALELFR (SEQ ID NO: 2) and LFTGHPETLEK (SEQ ID NO: 3), respectively, from the myoglobin protein. Each peptide produces a characteristic signature ion that can be used to detect and/or quantify myoglobin in a sample of cellular proteins. Providing both peptide internal standards together in an assay can provide an additional control for quantification.

Multiple peptide subsequences of a single protein may be synthesized, labeled, and fragmented to identify optimal fragmentation signatures. However, in one aspect at least two different peptides are used as internal standards to identify/quantify a single protein, providing an internal redundancy to any quantitation system (see, e.g., as shown in FIG. 6). In another aspect, peptide internal standards are synthesized which correspond to a single amino acid subsequence of a target polypeptide but which vary in one or more amino acids. The peptide internal standards may correspond to known variants or mutations in the target polypeptide or can be randomly varied to identify all possible mutations in an amino acid sequence.

In one preferred aspect, peptide internal standards corresponding to proteins expressed from nucleic acids comprising single nucleotide polymorphisms are synthesized to identify variant proteins encoded by such nucleic acids. Thus, peptide internal standards can be generated corresponding to SNP's which map to coding regions of genes and can be used to identify and quantify variant protein sequences on an individual or population level. SNP sequences can be accessed through The Human SNP database retrieved from http://www-genome.wi.mit.edu/SNP/human/index.html [on-line, retrieved on 2004-02-17].

Peptide internal standards may also be used to scan for mutations in proteins including, but not limited to, BRCA1, BRCA2, CFTR, p53, blood group antigens, HLA proteins, MHC proteins, G-Protein Coupled Receptors, apolipoprotein E, kinases (e.g., such as hCds1, MTKs, PTK, CDKs, STKs, CaMs, and the like) (see, e.g., U.S. Pat. No. 6,426,206), phosphatases, human drug metabolizing proteins, viral proteins such as a viral envelope proteins (e.g., HIV envelope proteins), transporter proteins, and the like.

In a further aspect, peptides corresponding to different modified forms of a protein are synthesized, providing internal standards to detect and/or quantitate changes in protein modifications in different cell states. In still a further aspect, peptide internal standards are generated which correspond to different proteins in a molecular pathway and/or modified forms of such proteins (e.g., proteins in a signal transduction pathway, cell cycle, metabolic pathway, blood clotting pathway, etc.) providing panels of internal standards to evaluate the regulated expression of proteins and/or the activity of proteins in a particular pathway. Combinations of the above-described internal standards can be used in a given assay.

Methods of Using Peptide Internal Standards

The labeled peptide internal standards according to the invention can be used to facilitate quantitative determination of the relative amounts of proteins in different samples. Also, the use of differentially isotopically labeled reagents as internal standards facilitates quantitative determination of the absolute amounts of one or more proteins present in a single sample. Samples that can be analyzed by method of the invention include, but are not limited to, cell homogenates; cell fractions; biological fluids, including, but not limited to urine, blood, and cerebrospinal fluid; tissue homogenates; tears; feces; saliva; lavage fluids such as lung or peritoneal lavages; and generally, any mixture of biomolecules, e.g., such as mixtures including proteins and one or more of lipids, carbohydrates, and nucleic acids such as obtained partial or complete fractionation of cell or tissue homogenates.

Preferably, a proteome is analyzed. By a proteome is intended at least about 20% of total protein coming from a biological sample source, usually at least about 40%, more usually at least about 75%, and generally 90% or more, up to and including all of the protein obtainable from the source. Thus, the proteome may be present in an intact cell, a lysate, a microsomal fraction, an organelle, a partially extracted lysate, biological fluid, and the like. The proteome will be a mixture of proteins, generally having at least about 20 different proteins, usually at least about 50 different proteins and in most cases, about 100 different proteins, about 1000 different proteins, about 10,000 different proteins, about 100,000 different proteins, or more. In one aspect, a proteome comprises substantially all of the proteins in a cell. In one preferred aspect, as shown in FIG. 4A, a complex mixture of cellular proteins is evaluated directly from a cell lysate, i.e., without any steps to separate and/or purify and/or eliminate cellular components or cellular debris.

While the methods described herein are compatible with any biochemical, immunological or cell biological fractionation methods that reduce sample complexity and enrich for proteins of low abundance, it is a particular advantage of the method that it can be used to detect and quantitate peptides in complex mixtures of polypeptides, such as cell lysates. Unlike methods in the prior art, because the present invention detects diagnostic signatures that are highly selective for individual peptides, the quantities of such peptides can be discerned even in a mixture of peptides of similar mass/charge ratios.

Generally, the sample will have at least about 0.01 mg of protein, at least about 0.05 mg, and usually at least about 1 mg of protein or 10 mg of protein or more, typically at a concentration in the range of about 0.1-10 mg/mi. The sample may be adjusted to the appropriate buffer concentration and pH, if desired.

Figure 4A:
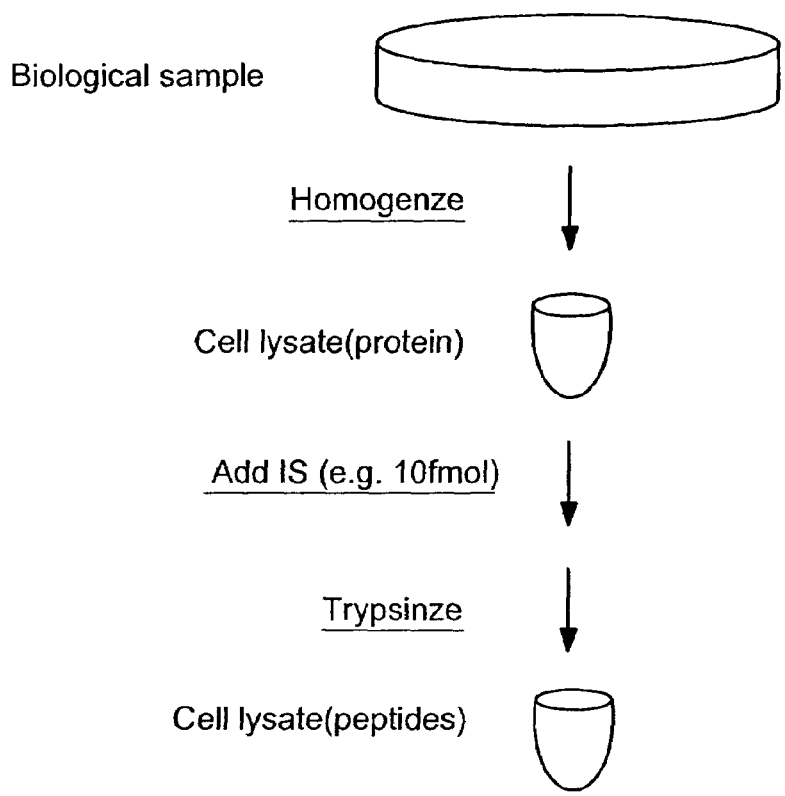
FIGS. 4A and B illustrate steps in a method for absolute quantitation of proteins in a complex mixture of proteins.

In one aspect, as shown in FIG. 4A, a known amount of a labeled peptide internal standard corresponding to a target protein to be detected and/or quantitated, is added to a sample such as a cell lysate. Preferably, about 10 femtomoles is spiked into the sample. The sample is contacted with a protease activity (e.g., one or more proteases or appropriate chemical agent(s) are added to the sample) and the spiked sample is incubated for a suitable period of time to allow peptide digestion. If the target protein is present in the sample, the digestion step should liberate a target peptide identical in sequence to the peptide portion of the internal standard and the amount of target peptides so liberated from target proteins in the sample should be proportional to the amount of target protein in the sample.

Preferably, a separation procedure is performed to separate a labeled peptide internal standard and corresponding target peptide from other peptides in the sample. Representative examples include high-pressure liquid chromatography (HPLC), Reverse Phase-High Pressure Liquid Chromatography (RP-HPLC), electrophoresis (e.g., capillary electrophoresis), anion or cation exchange chromatography, and open-column chromatography. Preferred is microcapillary liquid chromatography. As discussed above, internal standards are selected so that they co-elute with their corresponding target peptides as pairs of peptides that differ only in the mass contributed by the mass-altering label.

Figure 4B:
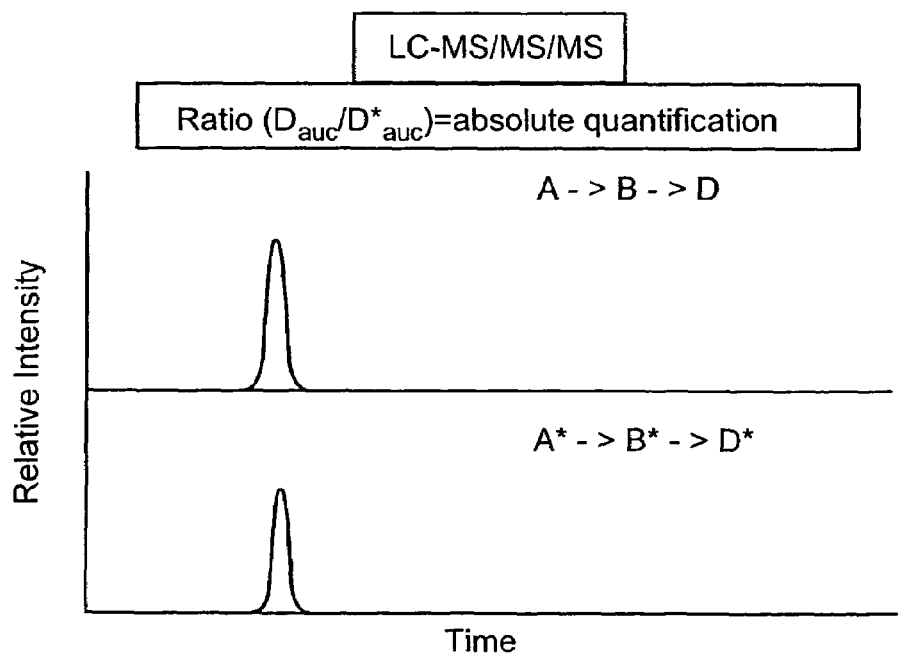
FIG. 4B shows mass spectra of a labeled peptide internal standard and the corresponding unlabeled peptide in the sample. The ratio of labeled to unlabeled peptide provides a means to quantify the amount of unlabeled peptide in the sample.

Each peptide then is examined by monitoring of a selected reaction in the mass spectrometer. This involves using the prior knowledge gained by the characterization of the peptide internal standard and then requiring the mass spectrometer to continuously monitor a specific ion in the MS/MS or MS" spectrum for both the peptide of interest and the internal standard. After elution, the areas-under-the-curve (AUC) for both the peptide internal standard and target peptide peaks are calculated (see, e.g., FIG. 4B). The ratio of the two areas provides the absolute quantification that can be normalized for the number of cells used in the analysis and the protein's molecular weight, to provide the precise number of copies of the protein per cell.

In one aspect, the presence and/or quantity of target polypeptide in a mixture is diagnostic of a cell state. In another aspect, the cell state is representative of an abnormal physiological response, for example, a physiological response which is diagnostic of a disease. In a further aspect, the cell state is a state of differentiation or represents a cell which has been exposed to a condition or agent (e.g., a drug, a therapeutic agent, a potential toxin). Preferably, protein quantities identified are compared to a reference quantity obtained from a reference sample (e.g., a sample from a normal patient, a sample not exposed to a condition or agent, etc.).

In another aspect, the method comprises determining the presence and/or quantity of target peptides in at least two mixtures. In still another aspect, one mixture is from a cell having a first cell state and the second mixture is from a cell having a second cell state. In a further aspect, the first cell is a normal cell and the second cell is from a patient with a disease. Preferably, first and second mixtures are evaluated in parallel.

Alternatively, the two mixtures can be from identical samples or cells. In one aspect, the labeled peptide internal standard is provided in different known amounts in each mixture. In another aspect, pairs of labeled peptide internal standards are provided each comprising mass-altering labels that differ in mass. For example, differentially labeled peptides may be generated by incorporating different amounts of a heavy label into each peptide varying the number of sites within the peptides labeled by a heavy isotope.

The invention also provides a method of determining the presence of and/or quantity of a modification in a target polypeptide. Preferably, the label in the internal standard is attached to a peptide comprising a modified amino acid residue or to an amino acid residue that is predicted to be modified in a target polypeptide. In one aspect, multiple internal standards representing different modified forms of a single protein and/or peptides representing different modified regions of the protein are added to a sample and corresponding target peptides (bearing the same modifications) are detected and/or quantified. Preferably, standards representing both modified and unmodified forms of a protein are provided in order to compare the amount of modified protein observed to the total amount of protein in a sample.

In another aspect, peptide internal standards comprising different peptides from a single protein are added in known amounts to a sample to provide additional controls or to scan for mutations in different regions of a protein. In a further aspect, peptides corresponding to a single amino acid subsequence in a protein but representing different variant forms of the protein are added to a sample as a means of detecting and/or quantifying a particular variant form of the protein.

In still another aspect, peptide internal standards are added to a sample that represents different proteins in a molecular pathway (e.g., a signal transduction pathway, a cell cycle, a metabolic pathway, a blood clotting pathway) and/or different modified forms of such proteins. In this aspect, the function of the pathway is evaluated by monitoring the presence, absence or quantity of particular pathway proteins and/or their modified forms. Multiple pathways may be evaluated at a time by combining mixtures of different pathway peptide internal standards.

In a further aspect, peptide internal standards represent proteins and/or modified forms thereof whose presence is diagnostic of a particular tissue type (e.g., neural proteins, cardiac proteins, skin proteins, lung proteins, liver proteins, pancreatic proteins, kidney proteins, proteins characteristic of reproductive organs, etc.). These can be used separately or in combination to perform tissue-typing analysis.

Peptide internal standards may represent proteins or modified forms thereof whose presence is characteristic of a particular genotype (e.g., such as HLA proteins, blood group proteins, proteins characteristic of a particular pedigree, etc.). These can be used separately or in combination to perform forensic analyses, for example.

In one aspect, peptide internal standards are used in prenatal testing to detect the presence of a congenital disease or to quantitate protein levels diagnostic of a chromosomal abnormality.

Peptide internal standards may represent proteins or modified forms thereof whose presence is characteristic of particular diseases. Such peptides may correspond to target proteins diagnostic of neurological disease (e.g., neurodegenerative diseases, including, but not limited to, Alzheimer's disease; amyotrophic lateral sclerosis; dementia, depression; Down's syndrome; Huntington's disease; peripheral neuropathy; multiple sclerosis; neurofibromatosis; Parkinson's disease; and schizophrenia). These standards can be used separately or in combination to diagnose a neurological disease.

Preferably, sets of internal standards are used so that diagnostic fragmentation signatures can be evaluated for a number of different diseases in a single assay. Thus, a sample may be obtained from a patient who presents with general symptoms associated with a neurological disease, and a peptide internal standard mixture comprising internal standards for proteins diagnostic of different neurological diseases can be added to the sample. The sample is contacted with a protease activity and peptide fractions are obtained, e.g., such as by HPLC. Peptide ions are subsequently fragmented as described above to detect any diagnostic fragmentation signatures present characteristic of a particular disease. The uniqueness of the fragmentation signature thus allows a specific diagnosis to be obtained while testing for a plurality of different types of diseases. The peptide internal standard mixture may include a peptide internal standard corresponding to a control target protein, such as a constitutively expressed protein of known abundance. A negative standard (e.g., such as a peptide internal standard corresponding to a plant protein) may also be provided.

Similarly, peptide internal standards can be used to diagnose an immune disease, including, but not limited to, acquired immunodeficiency syndrome (AIDS); Addison's disease; adult respiratory distress syndrome; allergies; ankylosing spondylitis; amyloidosis; anemia; asthma; atherosclerosis; autoimmune hemolytic anemia; autoimmune thyroiditis; bronchitis; cholecystitis; contact dermatitis; Crohn's disease; atopic dermatitis; dermatomyositis; diabetes mellitus; emphysema; episodic lymphopenia with lymphocytotoxins; erythroblastosis fetalis; erythema nodosum; atrophic gastritis; glomerulonephritis; Goodpasture's syndrome; gout; Graves' disease; Hashimoto's thyroiditis; hypereosinophilia; irritable bowel syndrome; myasthenia gravis; myocardial or pericardial inflammation; osteoarthritis; osteoporosis; pancreatitis; and polymyositis.

Similarly, peptide internal standards can be used to characterize infectious diseases, respiratory diseases, reproductive diseases, gastrointestinal diseases, dermatological diseases, hematological diseases, cardiovascular diseases, endocrine diseases, urological diseases, and the like.

Because peptide internal standards provide diagnostic fragmentation signatures for detecting and/or quantitating proteins or modified forms thereof, changes in the presence or amounts of such fragmentation signatures in a sample of proteins from a cell (e.g., such as a cell lystate), as discussed above, can be diagnostic of a cell state. In one aspect, a single fragmentation signature from a peptide internal standard is diagnostic. In other aspects, sets of fragmentation signatures are diagnostic and multiple peptide internal standards are spiked into a sample to evaluate changes in cell state.

In one preferred embodiment, changes in cell state are evaluated after exposure of the cell to a compound. Compounds are selected which are capable of normalizing a cell state, e.g., by selecting for compounds which alter fragmentation signatures from those characteristic of abnormal physiological responses to those representative of a normal cell.

For example, a three way comparison of healthy, diseased, and treated diseased individuals can identify which compounds are able to restore a disease cell state to a one that more closely resembles a normal cell state. This can be used to screen for drugs or other therapeutic agents, to monitor the efficacy of treatment, and to detect or predict the occurrence of side effects, whether in a clinical trial or in routine treatment, and to identify protein targets which are more important to the manifestation and treatment of a disease.

Compounds which can be evaluated include, but are not limited to: drugs; toxins; proteins; polypeptides; peptides; amino acids; antigens; cells, cell nuclei, organelles, portions of cell membranes; viruses; receptors; modulators of receptors (e.g., agonists, antagonists, and the like); enzymes; enzyme modulators (e.g., such as inhibitors, cofactors, and the like); enzyme substrates; hormones; nucleic acids (e.g., such as oligonucleotides; polynucleotides; genes, cDNAs; RNA; antisense molecules, ribozymes, aptamers), and combinations thereof. Compounds also can be obtained from synthetic libraries from drug companies and other commercially available sources known in the art (e.g., including, but not limited to the LEADQUEST®, library of screening compounds) or can be generated through combinatorial synthesis using methods well known in the art. In one aspect, a compound is identified as a modulating agent if it alters the site of modification of a polypeptide and/or if it alters the amount of modification by an amount that is significantly different from the amount observed in a control cell (e.g., not treated with compound) (setting p values to<0.05). In another aspect, a compound is identified as a modulating agent, if it alters the amount of the polypeptide (whether modified or not).

Compounds identified as modulating agents are used in methods of treatment of pathologies associated with abnormal sites/levels of modification or abnormal levels or types of protein. For administration to a patient, one or more such compounds are generally formulated as a pharmaceutical composition. Preferably, a pharmaceutical composition is a sterile aqueous or non-aqueous solution, suspension or emulsion, which additionally comprises a physiologically acceptable carrier (i.e., a non-toxic material that does not interfere with the activity of the active ingredient). More preferably, the composition also is non-pyrogenic and free of viruses or other microorganisms. Any suitable carrier known to those of ordinary skill in the art may be used. Representative carriers include, but are not limited to: physiological saline solutions, gelatin, water, alcohols, natural or synthetic oils, saccharide solutions, glycols, injectable organic esters such as ethyl oleate or a combination of such materials. Optionally, a pharmaceutical composition may additionally contain preservatives and/or other additives such as, for example, antimicrobial agents, anti-oxidants, chelating agents and/or inert gases, and/or other active ingredients.

Routes and frequency of administration, as well doses, will vary from patient to patient. In general, the pharmaceutical compositions is administered intravenously, intraperitoneally, intramuscularly, subcutaneously, intracavity or transdermally. Between 1 and 6 doses is administered daily. A suitable dose is an amount that is sufficient to show improvement in the symptoms of a patient afflicted with a disease associated an aberrant modification state or an abnormal level or type of a protein. Such improvement may be detected by monitoring appropriate clinical or biochemical endpoints as is known in the art. In general, the amount of a modulating agent present in a dose, or produced in situ by DNA present in a dose (e.g., where the modulating agent is a polypeptide or peptide encoded by the DNA), ranges from about 1 µg to about 100 mg per kg of host. Suitable dose sizes will vary with the size of the patient, but will typically range from about 10 mL to about 500 mL for 10-60 kg animal. A patient can be a mammal, such as a human, or a domestic animal.

Computer Systems and Databases

The invention also provides methods for generating a database comprising data files for storing information relating to diagnostic fragmentation signatures for peptide internal standards. Preferably, data in the data files include one or more peptide fragmentation signatures characteristic or diagnostic of a cell state (e.g., such as a state which is characteristic of a disease, a normal physiological response, a developmental process, exposure to a therapeutic agent, exposure to a toxic agent or a potentially toxic agent, and/or exposure to a condition). Data in the data files also preferably includes values corresponding to level of proteins corresponding to the peptide fragmentation signatures found in a particular cell state.

In one aspect, for a cell state determined by the differential expression of at least one protein, a data file corresponding to the cell state will minimally comprise data relating to the mass spectra observed after peptide fragmentation of a peptide internal standard diagnostic of the protein. Preferably, the data file will include a value corresponding to the level of the protein in a cell having the cell state. For example, a tumor cell state is associated with the overexpression of p53 (see, e.g., Kern, et al., Int. J. Oncol. 21(2): 243-9, 2001). The data file will comprise mass spectral data observed after fragmentation of a labeled peptide internal standard corresponding to a subsequence of p53. Preferably, the data file also comprises a value relating to the level of p53 in a tumor cell. The value may be expressed as a relative value (e.g., a ratio of the level of p53 in the tumor cell to the level of p53 in a normal cell) or as an absolute value (e.g., expressed in nM or as a % of total cellular proteins).

Preferably, the data files also include information relating to the presence or amount of a modified form of a target a polypeptide in at least one cell and to mass spectral data diagnostic of the modified form (i.e., peak data for a fragmented peptide internal standard which corresponds to the modified form). More preferably, the data files also comprise spectral data diagnostic of the unmodified form as well as data corresponding to the level of the unmodified form.

In one aspect, the database also comprises data relating to the source of a cell whose cell state is being evaluated. For example, the database comprises data relating to identifying characteristics of a patient from whom the cell is derived.

The invention further provides a computer memory comprising data files for storing information relating to the diagnostic fragmentation signatures of peptide internal standards. In one preferred aspect, the database comprises peptide diagnostic signatures, e.g., mass spectral data obtained after fragmentation of one or more peptide internal standards, which can be used to identify a cell having a particular cell state. More preferably, the database includes data relating to a plurality of cell state profiles, i.e., data relating to levels of target proteins identified by the peptide internal standards in a plurality of cells having different cell states. For example, profiles of disease states may be included in the database and these profiles will include measurements of levels of one or more proteins, or modified forms thereof, characteristic of the disease state. Profiles of cells exposed to different compounds include measurements of levels of proteins or modified forms thereof characteristic of the response(s) of the cells to the compounds. In one aspect, the measurements are obtained by performing any of the methods described above.

Preferably, the database is in electronic form and the cell state profiles, which are also in electronic form, provide measurements of levels of a plurality of proteins in a cell or cells of one or more subjects. In one aspect, the database comprises measurements of more than about 5, more than about 10, more than about 30, more than about 50, more than about 100, more than about 500, more than about 1000, more than about 10,000, or more than about 100,000 proteins in a cell, i.e., the database comprises data relating to the proteome of a cell. The measurements represent levels of modified and/or unmodified forms of the proteins. In one aspect, the measurements also include data regarding the site of protein modifications in one or more proteins in a cell.

In one preferred aspect, cell state profiles comprise quantitative data relating to target proteins and/or modified forms thereof obtained by using one or more of the methods described above.

A variety of data storage structures are available for creating a computer readable medium or memory comprising data files of the database. The choice of the data storage structure will generally be based on the means chosen to access the stored information. For example, the data can be stored in a word processing text file, formatted in commercially-available software such as WordPerfect and Microsoft Word, or represented in the form of an ASCII file, stored in a database application, such as DB2, Sybase, Oracle, or the like. The skilled artisan can readily adapt any number of data processor structuring formats (e.g., text files, pdf files, or database structures) in order to obtain computer readable medium or a memory having recorded thereon data relating to diagnostic fragmentation signatures, e.g., such as mass spectral data obtained after fragmentation of the peptide internal standards, and protein levels.

Correlations between a particular diagnostic signature observed and a cell state (e.g., a disease, genotype, tissue type, etc.) may be known or may be identified using the database described above and suitable statistical programs, expert systems, and/or data mining systems, as are known in the art.

In another aspect, the invention provides a computer system comprising: a database having data files containing information identifying diagnostic fragmentation signatures (e.g., mass spectral peaks) as corresponding to particular peptide internal standards which in turn are identified as corresponding to particular target proteins. Preferably, the data files also comprise information for relating the diagnostic fragmentation signatures so identified to one or more cell states, e.g., where the target protein corresponding to the peptide internal standard is diagnostic of a cell state, the peptide internal standard and fragmentation signature are also identified within the data file as being diagnostic of a cell state. In one preferred aspect, the system further comprises a user interface allowing a user to selectively view information relating to a diagnostic fragmentation signature and to obtain information about a cell state. The interface may comprise links allowing a user to access different portions of the database by selecting the links (e.g. by moving a cursor to the link and clicking a mouse or by using a keystroke on a keypad). The interface may additionally display fields for entering information relating to a sample being evaluated.

Still more preferably, the system is capable of comparing diagnostic fragmentation signatures of known peptide internal standards to mass spectral data obtained for peptides in a sample spiked with one or more internal standards in order to determine and/or quantify levels of target proteins corresponding to the standards in the sample. When a match is identified, the system may also provide information regarding the cell state for which the peptide internal standard is diagnostic (i.e., the system will identify the source of the cell, the compound to which a cell has been exposed, and/or a disease which the cell is responding to). In some aspects, sets of peptide internal standards are evaluated, as only the set will be diagnostic.

The system may also be used to collect and categorize peptide fragmentation signatures for different types of cell states to identify sets of peptide internal standards characteristic of particular cell states. In this aspect, preferably, the system comprises a relational database. More preferably, the system further comprises an expert system for identifying sets of peptide internal standards that are diagnostic of different cell states. In one aspect, the system is capable of clustering related information. Suitable clustering programs are known in the art and are described in, for example, U.S. Pat. No. 6,303,297.

The system preferably comprises a means for linking a database comprising data files of diagnostic fragmentation signatures to other databases, e.g., such as genomic databases, pharmacological databases, patient databases, proteomic databases, and the like.

Preferably, the system comprises in combination, a data entry means, a display means (e.g., graphic user interface); a programmable central processing unit; and a data storage means comprising the data files and information described above, electronically stored in a relational database.

Preferably, the central processing unit comprises an operating system for managing a computer and its network interconnections. This operating system can be, for example, of the Microsoft Windows' family, such as Windows 95, Windows 98, or Windows NT, or any new Windows programmed developed. A software component representing common languages may be provided. Preferred languages include C/C++, and JAVA®. In one aspect, methods of this invention are programmed in software packages which allow symbolic entry of equations, high-level specification of processing, and statistical evaluations.

Reagents and Kits

The invention further provides reagents useful for performing the method. In one aspect, a reagent according to the invention comprises a peptide internal standard labeled with a stable isotope. Preferably, the standard has a unique peptide fragmentation signature diagnostic of the peptide. The peptide is a subsequence of a known protein and can be used to identify the presence of and/or quantify the protein in sample, such as a cell lysate.

The invention additionally provides kits comprising one or more peptide internal standards labeled with a stable isotope or reagents suitable for performing such labeling. In certain preferred embodiments, the method utilizes isotopes of hydrogen, nitrogen, oxygen, carbon, or sulfur. Suitable isotopes include, but are not limited to, $^2$H, $^{13}$C, $^{15}$N, $^{17}$O, 18O, or 34S. In another aspect, pairs of peptide internal standards are provided, comprising identical peptide portions but distinguishable labels, e.g., peptides may be labeled at multiple sites to provide different heavy forms of the peptide. Pairs of peptide internal standards corresponding to modified and unmodified peptides also can be provided.

In one aspect, a kit comprises peptide internal standards comprising different peptide subsequences from a single known protein. In another aspect, the kit comprises peptide internal standards corresponding to different known or predicted modified forms of a polypeptide. In a further aspect, the kit comprises peptide internal standards corresponding to sets of related proteins, e.g., such as proteins involved in a molecular pathway (a signal transduction pathway, a cell cycle, etc), or which are diagnostic of particular disease states, developmental stages, tissue types, genotypes, etc. Peptide internal standards corresponding to a set may be provided in separate containers or as a mixture or "cocktail" of peptide internal standards.

In one aspect, a plurality of peptide internal standards representing a MAPK signal transduction pathway is provided. Preferably, the kit comprises at least two, at least about 5, at least about 10 or more, of peptide internal standards corresponding to any of MAPK, GRB2, mSOS, ras, raf, MEK, p85, KHS1, GCK1, HPK1, MEKK 1-5, ELK1, c-JUN, ATF-2, 3APK, MLK1-4, PAK, MKK, p38, a SAPK subunit, hsp27, and one or more inflammatory cytokines.

In another aspect, a set of peptide internal standards is provided which comprises at least about two, at least about 5 or more, of peptide internal standards which correspond to proteins selected from the group including, but not limited to, PLC isoenzymes, phosphatidylinositol 3-kinase (PI-3 kinase), an actin-binding protein, a phospholipase D isoform, (PLD), and receptor and nonreceptor PTKs.

In another aspect, a set of peptide internal standards is provided which comprises at least about 2, at least about 5, or more, of peptide internal standards which correspond to proteins involved in a JAK signaling pathway, e.g., such as one or more of JAK 1-3, a STAT protein, IL-2, TYK2, CD4, IL-4, CD45, a type I interferon (IFN) receptor complex protein, an IFN subunit, and the like.

In a further aspect, a set of peptide internal standards is provided which comprises at least about 2, at least about 5, or more of peptide internal standards which correspond to cytokines. Preferably, such a set comprises standards selected from the group including, but not limited to, pro-and anti-inflammatory cytokines (which may each comprise their own set or which may be provided as a mixed set of peptide internal standards).

In still another aspect, a set of peptide internal standards is provided which comprises a peptide diagnostic of a cellular differentiation antigen or CD. Such kits are useful for tissue typing.

In one aspect, peptides corresponding to known variants or mutations in a target polypeptide, or which are randomly varied to identify all possible mutations in an amino acid sequence, are provided in the kit. In a preferred aspect, peptide internal standards corresponding to proteins expressed from nucleic acids comprising single nucleotide polymorphisms are provided.

Peptide internal standards may include peptides corresponding to variant proteins selected from the group consisting of BRCAI; BRCA2; CFTR; p53; a JAK protein; a STAT protein; blood group antigens; HLA proteins; MHC proteins; G-Protein Coupled Receptors; apolipoprotein E; kinases (e.g., such as hCdsl, MTKs, PTK, CDKs, STKs, CaMs, and the like) (see, e.g., U.S. Pat. No. 6,426,206); phosphatases; human drug metabolizing proteins; viral proteins, including but not limited to viral envelope proteins (e.g., an HIV envelope protein); transporter proteins; and the like.

In one aspect, the peptide internal standard comprises a label associated with a modified amino acid residue, such as a phosphorylated amino acid residue, a glycosylated amino acid residue, an acetylated amino acid residue, a farnesylated residue, a ribosylated residue, and the like. In another aspect, a pair of reagents is provided, a peptide internal standard corresponding to a modified peptide and a peptide internal standard corresponding to a peptide, identical in sequence but not modified.

In another aspect, one or more control peptide internal standards are provided. For example, a positive control may be a peptide internal standard corresponding to a constitutively expressed protein, while a negative peptide internal standard may be provided corresponding to a protein known not to be expressed in a particular cell or species being evaluated. For example, in a kit comprising peptide internal standards for evaluating a cell state in a human being, a plant peptide internal standard may be provided.

In still another aspect, a kit comprises a labeled peptide internal standard as described above and software for analyzing mass spectra (e.g., such as SEQUEST).

Preferably, the kit also comprises a means for providing access to a computer memory comprising data files storing information relating to the diagnostic fragmentation signatures of one or more peptide internal standards. Access may be in the form of a computer readable program product comprising the memory, or in the form of a URL and/or password for accessing an internet site for connecting a user to such a memory. In another aspect, the kit comprises diagnostic fragmentation signatures (e.g., such as mass spectral data) in electronic or written form, and/or comprises data, in electronic or written form, relating to amounts of target proteins characteristic of one or more different cell states and corresponding to peptides which produce the fragmentation signatures.

The kit may further comprise expression analysis software on computer readable medium, which is capable of being encoded in a memory of a computer having a processor and capable of causing the processor to perform a method comprising: determining a test cell state profile from peptide fragmentation patterns in a test sample comprising a cell with an unknown cell state or a cell state being verified; receiving a diagnostic profile characteristic of a known cell state; and comparing the test cell state profile with the diagnostic profile.

In one aspect, the test cell state profile comprises values of levels of peptides in a test sample that correspond to one or more peptide internal standards provided in the kit. The diagnostic profile comprises measured levels of the one or more peptides in a sample having the known cell state (e.g., a cell state corresponding to a normal physiological response or to an abnormal physiological response, such as a disease).

Preferably, the software enables a processor to receive a plurality of diagnostic profiles and to select a diagnostic profile that most closely resembles or "matches" the profile obtained for the test cell state profile by matching values of levels of proteins determined in the test sample to values in a diagnostic profile, to identify substantially all of a diagnostic profile which matches the test cell state profile.

Substantially all of a diagnostic profile is matched by a test cell state profile when most of the cellular constituents (e.g., proteins in the proteome) which are diagnostic of the cell state, are found to have substantially the same value in the two profiles within a margin provided by experimental error. Preferably, at least about 75% of the diagnostic proteins can be matched, at least about 80%, at least about 85%, at least about 90% or at least about 95% can be matched. Preferably, where one, or only a few proteins (e.g., less than 10) are used to establish s diagnostic profile, preferably all of the proteins have substantially the same value.

Variations, modifications, and other implementations of what is described herein will occur to those of ordinary skill in the art without departing from the spirit and scope of the invention as described and claimed herein and such variations, modifications, and implementations are encompassed within the scope of the invention.

All of the references identified hereinabove are expressly incorporated herein by reference.

What is claimed is:

1. A method for determining the presence and/or quantity of a modified target polypeptide in at least one mixture of different polypeptides, comprising:

a) providing a mixture of different polypeptides;

b) adding a known quantity of a single peptide internal standard labeled with a mass-altering label, thereby generating a spiked mixture, wherein the labeled peptide internal standard comprises a subsequence of the target polypeptide and wherein the labeled peptide internal standard possesses a known peptide fragment signature diagnostic of the presence of the peptide;

c) treating the spiked mixture with a protease activity to generate a plurality of peptides including the labeled peptide internal standard and peptides corresponding to the target polypeptide;

d) fragmenting the labeled peptide internal standard and any target peptide present in the spiked mixture comprising the same amino acid sequence as the labeled peptide internal standard;

e) determining the ratio of labeled fragments to unlabeled fragments; and f) calculating from the ratio and the known quantity of the labeled internal standard, the quantity of the target polypeptide in the mixture.

2. The method of claim 1, wherein the fragmenting is performed by multistage mass spectrometry.

3. The method of claim 1, further comprising separating peptides obtained in step (c) using a chromatography step.

4. The method according to claim 3, wherein the chromatography step comprises performing HPLC.

5. The method according to claim 4, wherein the labeled peptide internal standard and target peptide comprising the same amino acid sequences as the labeled peptide internal standard are co-eluted during separation.

6. The method according to claim 1, wherein the mixture of different polypeptides is selected from the group consisting of: a crude fermenter solution, a cell-free culture fluid, a cell or tissue extract, blood sample, a plasma sample, a lymph sample, a cell or tissue lysate; a mixture comprising at least about 100 different polypeptides; a mixture comprising substantially the entire complement of proteins in a cell or tissue.

7. The method according to claim 1, wherein the peptide internal standard is labeled using a stable isotope.

8. The method according to claim 1, wherein the labeled peptide internal standard is produced according to a method for generating a peptide internal standard, comprising:
   a) identifying a real or predicted peptide digestion product of a target polypeptide;
   b) determining the amino acid sequence of the peptide;
   c) synthesizing a peptide comprising the amino acid sequence of the peptide digestion product;
   d) labeling the peptide with a mass-altering label;
   e) fragmenting the peptide and identifying a peptide signature diagnostic of the peptide.

9. The method according to claim 1, wherein the presence and/or quantity of target polypeptide is diagnostic of a cell state.

10. The method according to claim 9, wherein the cell state is representative of an abnormal physiological response.

11. The method according to claim 10, wherein the abnormal physiological response is diagnostic of a disease.

12. The method according to claim 9, wherein the cell state is a state of differentiation.

13. The method according to claim 1, further comprising determining the presence and/or quantity of target peptides in at least two mixtures.

14. The method according to claim 13, wherein one mixture is from a cell having a first cell state and the second mixture is from a cell having a second cell state.

15. The method according to claim 14, wherein the first cell is a normal cell and the second cell is from a patient with a disease.

16. The method according to claim 13, wherein the determining is done in parallel.

17. The method according to claim 13, wherein the two mixtures are the same arid the labeled peptide internal standard is provided in different known amounts in each mixture.

18. The method according to claim 13, wherein the labeled peptide internal standard in each mixture comprises the same peptide but different labels.

* * * * *

```
SEQUENCE LISTING

<160> NUMBER OF SEQ ID NOS: 5

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: May be (pT)
<220> FEATURE:
<221> NAME/KEY: MOD_RES
<222> LOCATION: (6)
<223> OTHER INFORMATION: May be (mK) and/or radiolabeled

<400> SEQUENCE: 1

Gly Phe Thr Ala Leu Lys
 1               5

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ala Leu Glu Leu Phe Arg
 1               5

<210> SEQ ID NO 3
```

```
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Leu Phe Thr Gly His Pro Glu Thr Leu Glu Lys
 1               5                  10

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Leu Ser Phe Val Phe Gly Gly Thr Asp Glu Lys
 1               5                  10

<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Radiolabeled Phe
<220> FEATURE:
<221> NAME/KEY: MOD_RES
<222> LOCATION: (5)
<223> OTHER INFORMATION: Radiolabeled Phe

<400> SEQUENCE: 5

Leu Ser Phe Val Phe Gly Gly Thr Asp Glu Lys
 1               5                  10
```